(12) United States Patent
Chu et al.

(10) Patent No.: US 8,110,035 B2
(45) Date of Patent: Feb. 7, 2012

(54) INTEGRATED PORCELAIN SYSTEM FOR A DENTAL PROSTHESIS

(75) Inventors: Christopher Chu, West Windsor, NJ (US); Slawomir Banasiak, Kearny, NJ (US); Victoriya Shtessel-Nemzer, Newtown, PA (US)

(73) Assignee: DENTSPLY International Inc., York, PA (US)

( * ) Notice: Subject to any disclaimer, the term of this patent is extended or adjusted under 35 U.S.C. 154(b) by 785 days.

(21) Appl. No.: 12/156,169

(22) Filed: May 30, 2008

(65) Prior Publication Data

US 2009/0298016 A1 Dec. 3, 2009

(51) Int. Cl.
*A61K 6/02* (2006.01)

(52) U.S. Cl. ......... 106/35; 501/14; 501/17; 501/21; 501/29; 501/69; 501/70; 433/222.1; 433/202.1; 433/212.1

(58) Field of Classification Search .......... 106/35; 433/222.1, 202.1, 212.1; 501/14, 17, 21, 501/29, 69, 70
See application file for complete search history.

(56) References Cited

U.S. PATENT DOCUMENTS

| 4,741,699 | A | | 5/1988 | Kosmos | |
|---|---|---|---|---|---|
| 5,281,563 | A | | 1/1994 | Kamma et al. | |
| 5,653,791 | A | * | 8/1997 | Panzera et al. | 106/35 |
| 6,120,591 | A | * | 9/2000 | Brodkin et al. | 106/35 |
| 6,428,614 | B1 | | 8/2002 | Brodkin et al. | |
| 2007/0196788 | A1 | * | 8/2007 | Chu et al. | 433/202.1 |

FOREIGN PATENT DOCUMENTS

WO WO 2006/055800 5/2006

* cited by examiner

*Primary Examiner* — Carol M Koslow
(74) *Attorney, Agent, or Firm* — Douglas J. Hura; David A. Zdurne; Leana Levin

(57) ABSTRACT

An integrated dental porcelain system for making dental prostheses and restorations is provided. The system includes three universal major components: a) opaque porcelain composition; b) pressable dentin ingot; and c) veneering porcelain composition that can be used interchangeably for making restorations. Techniques for making the prostheses and restorations include porcelain fused-to-metal (PFM), press-to-metal (PTM), and either pressed and/or machined all-ceramic methods. The system uses both a hand-layering of veneering porcelain (PFM technique) and a hot-pressing process (PTM and all-ceramic technique) to fabricate the prostheses and restorations.

11 Claims, 3 Drawing Sheets

INTEGRATED PORCELAIN SYSTEM FOR A DENTAL PROSTHESIS

BACKGROUND OF THE INVENTION

1. Field of the Invention

The invention relates generally to materials for making dental prostheses and restorations such as inlays, onlays, veneers, crowns, and bridges. Particularly, the materials include one universal opaque, one universal pressable ingot, and one universal veneering porcelain that can be used interchangeably to manufacture a prosthesis or restoration using different techniques. This includes porcelain-fused-to-metal (PFM), press-to-metal (PTM), and pressed or computer-aided-manufacturing (CAM) machined all-ceramic techniques.

2. Brief Description of the Related Art

There are various methods known in the dental arts for making dental prostheses and restorations. By the term, "prosthesis" or "restoration" as used herein, it is meant any product that replaces or restores lost tooth structure, teeth, or oral tissue including, but not limited to, implant stents, bite registrations, crown and bridges, fillings, baseplates, splints, denture liners, custom trays, artificial teeth, repairs for natural teeth, veneers, denture repairs, denture relines, retainers, orthodontic components, provisional dental devices, inlays, onlays, orthodontic appliances, temporary dentures, temporary partial dentures, maxillofacial prostheses, obturators, and occular prostheses, and the like.

Conventional dental prostheses may include a metal coping or substructure to provide additional mechanical strength and durability to the prosthesis. In practice, the metal copings are covered with glass or ceramic-based materials that mimic the color and form of natural teeth. The metal copings support the glass or ceramic-based veneering layer and provide enhanced structural strength and toughness to the restoration.

A traditional method for making a dental prosthesis is known as "porcelain-fused-to-metal" (PFM). Typically, the process of making a PFM restoration involves applying three layers of porcelain onto a metal framework. Initially, an opaque porcelain composition, in either powder or paste form, is applied over a metal framework to form an opaque layer that masks the metal. Subsequently, a dentin body layer is built up using dentin porcelain powder and then a third layer simulating the incisal portion of a natural tooth is built up using enamel porcelain powder. In PFM restorations, the layering of the wet porcelain compositions is traditionally done by hand. The porcelain compositions are fired at high temperatures to form hard and durable dentin and incisal layers having the appearance of natural teeth. Other porcelain materials, such as opaceous dentin, dentin modifier, and stain porcelain, margin, and final margin porcelains can be added to enhance the esthetics of the final dental restoration. The PFM restorations can be finished by applying a thin layer of glaze porcelain to provide a glossy surface finish.

One drawback with PFM restorations is that the dark-colored margin may be exposed at the gum line and the restoration may not have the most pleasing esthetics. To improve esthetics, "all-ceramic" systems have been developed. These all-ceramic systems use a ceramic core in place of the metal framework. The ceramic core is coated with at least one porcelain layer. In one technique, an all-ceramic prosthesis having a core is fabricated using a hot-pressing technique. (For example, the Empress™ prosthetic system (Ivoclar Vivadent AG, Liechtenstein) was developed.) An alternative way of fabricating all-ceramic cores is to use a computer-aided-manufacturing (CAM) method and machine directly on a ceramic block as described in the Cerec™ system (Sirona Dental Systems GmbH, Germany). While all-ceramic prostheses may offer improved esthetics over PFM restorations, the all-ceramic prostheses tend to be more brittle. Traditionally, all-ceramic prostheses have been limited generally to anterior up to pre-molar applications. Although in recent years, using high strength alumina and zirconia as the core has allowed all-ceramic restorations to be used in posterior and bridge applications.

Another method that has grown in popularity over the last several years is known as the "press-to-metal" (PTM) process. The PTM process involves placing a metal coping or substructure in a mold. The coping is then coated with an opaque porcelain composition which may be in powder or paste form. The opaque coating is followed by wax-up and spruing to form the prosthesis form. The form is then invested in a ceramic investment material, and the wax is burned out. This forms the prosthesis mold. A porcelain layer is fused to the opaque surface by hot-pressing an ingot porcelain material onto the coping contained in the mold at fusing temperatures. The hot-pressed porcelain flows into the burn-out cavity to form the dentin layer. The prosthesis is then divested of the molding material and finished. The result is a strong and tough dental prosthesis having a metal substructure that is veneered with porcelain. The prosthesis has generally good esthetics with integrated transparency that matches the appearance of natural dentition.

Conventional methods for making PFM, PTM, and all-ceramic restorations are described in the patent literature. For example, Kosmos, U.S. Pat. No. 4,741,699 discloses making a porcelain dental restoration having fluorescence that matches the fluorescence of natural teeth. The restoration includes a metal supporting substrate, a body layer, and incisal layer. An aqueous slurry of an opaque porcelain is applied and fired to the metal substrate. A body layer and incisal layer are formed from porcelain powder mixtures containing fluorescent pigment. The powder mixtures comprise a base porcelain, stained porcelain, and fluorescing agent and are applied by hand to build-up the restoration.

Komma et al., U.S. Pat. No. 5,281,563 describes methods for making metal and ceramic dentures. The ceramic powder is applied to the metallic framework as an aqueous slurry and fired at elevated temperatures to produce the prosthesis. Komma notes that it is important that the firing temperature (processing temperature) of the ceramic body be at least 100° C. below the solidus temperature of the material in the metallic framework and the coefficient of thermal expansion of the ceramic body be only very slightly less than that of the metallic material, so that no cracks are produced in the lining layer during firing and cooling down.

Brodkin et al., U.S. Pat. No. 6,428,614 is directed to an opaque porcelain material for making both all-ceramic and porcelain-fused-to-metal (PFM) restorations. The opaque porcelain exhibits a coefficient of thermal expansion (CTE) substantially equal to or slightly above the CTE of the metal to which the porcelain is being applied. The porcelain material is fabricated from a mixture of two frit compositions. The porcelain material has a composition of 48 to 65% $SiO_2$; 10 to 15% $Al_2O_3$; 0.5 to 2% CaO; 1.5 to 3% $Li_2O$; 15 to 17% $K_2O$; 4 to about 6% $Na_2O$; and 0.4 to 1% F.

Chu and Banasiak, US Patent Application Publication No. US 2007/0196788 discloses a dental prosthesis having a metal coping that is coated with an opaque coating. A single porcelain layer having an integrated tooth-like translucency is coated over the opaque coating. The porcelain layer is formed of a dentin frit and enamel frit that is sintered into an ingot shape. The weight percent of dentin frit is in the range of 70 to 85% and the weight percent of enamel frit is in the range of 15 to 30%. The resulting restoration has strong substructure that is veneered with porcelain having an integrated transparency.

One major problem with conventional PFM, PTM, and all-ceramic systems available in the marketplace today is that the components of each system are tailored to their own applications. The materials cannot be used interchangeably across the systems due to the thermal incompatibility among the components and/or metal substructure. Hence, systems with various components need to be purchased separately for making different types of restorations. This may cause over-inventory problems and confusion over mixing use of the components in dental laboratories.

It is an object of the present invention to provide an integrated porcelain system having components that can be used interchangeably among porcelain-fused-to metal (PFM), press-to-metal (PTM), and pressed or computer-aided-manufacturing (CAM) machined all-ceramic restorations It is another object of the invention to provide a universal opaque porcelain composition that can be used for making PFM and PTM prostheses. Yet another object of the invention is to provide universal pressable ingots that can be used for making dentin body layers over opaqued metal framework in PTM prostheses and all-ceramic cores. It is still another object of the invention to provide a universal veneering porcelain composition that can be used for making dentin-enamel layers and enamel layers. These and other objects, features, and advantages of the present invention are evident from the following description and illustrated embodiments.

SUMMARY OF THE INVENTION

The present invention provides an integrated dental porcelain system for making dental prostheses and restorations. The system includes three universal major components: a) opaque porcelain composition; b) pressable dentin ingot; and c) veneering porcelain composition that can be used interchangeably for making porcelain fused-to-metal (PFM), press-to-metal (PTM), and either pressed and/or machined all-ceramic restorations. The system uses both a hand-layering of veneering porcelain (PFM) and a hot-pressing process (PTM & all-ceramic) to fabricate a prosthesis or restoration for the patient.

BRIEF DESCRIPTION OF THE DRAWINGS

The novel features that are characteristic of the present invention are set forth in the appended claims. However, the preferred embodiments of the invention, together with further objects and attendant advantages, are best understood by reference to the following detailed description in connection with the accompanying drawings in which:

DETAILED DESCRIPTION OF THE PREFERRED EMBODIMENTS

Figure 1:
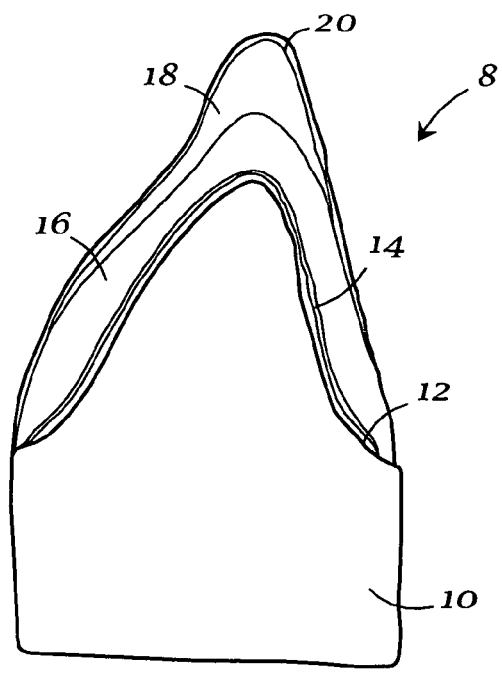
FIG. 1 is a cross-sectional schematic view of a PFM crown on a die model fabricated with components in accordance with the invention.

The present invention relates to materials, methods, and kits for making dental prostheses. The materials of this invention which may be supplied as components of a kit, can be used to provide porcelain/metal restorations, using either hand layering of veneering porcelain (PFM) or a pressing process (PTM) to apply a finished surface, along with all-ceramic restorations.

The materials for making the dental prostheses in accordance with this invention include principally: (1) universal opaquing porcelains, in either powder or paste form, for masking the surface of metal framework that would otherwise be visible through the porcelain veneer. This is used for making both PFM and PTM restorations; (2) universal pressable ingots for pressing dentin body over opaqued metal framework to make PTM restorations or for pressing a stand-alone all-ceramic core; and (3) universal dentin/enamel porcelain for building incisal layer in making either PFM, PTM, and/or all-ceramic (either pressed or machined) restorations. These materials can be supplied in a kit to a dental laboratory for making the dental prostheses.

In addition, the kit may include a shade stain porcelain paired with a glaze porcelain for shading and finishing either full-contour PTM and/or all-ceramic restorations. The applied shade stain and glaze porcelain compositions are fired in a single step. Also, the same glaze porcelain can be used for finishing PFM, incisal cutback PTM, and all-ceramic restorations in accordance with this invention. Further, the kit may include other porcelain materials such as opaceous dentin, dentin modifier, correction, margin, and final margin porcelain for finishing the prosthesis, as necessary. The different components of the kit are discussed in further detail below.

Universal Opaque Porcelain

The universal opaque porcelain composition is used for coating the metal substructure of the prosthesis. The opaque coating masks the metal substructure and prevents the dark-colored surface and edges of the substructure from being visible. This coating step results in an "opaqued" metal substructure. The opaque porcelain can be applied over the metal substructure in powder or paste form. The opaque porcelain can be applied by spraying, slurry dip, electro-depositing, or other methods known to those skilled in the art. Then, the composition is fired to form a hard and durable coating. The firing temperature of the opaque porcelain is preferably between 800° C. and 1000° C., more preferably between 830° C. and 930° C., and most preferably between 860° C. and 900° C.

The opaque coating, which forms as a result of this firing step, has thermal compatibility and thermal stability with a later applied porcelain veneer layer. By the term, "thermal compatibility" or "thermally compatible" with respect to the opaque coating, it is meant that no substantial cracks are visible in the coating after firing at a temperature between 800° C. and 1000° C. upon examining the coating under an optical microscope (10× magnification); and no substantial cracks, are visible in the porcelain veneer layer after firing at a temperature between 700° C. and 1000° C. upon examining the layer under an optical microscope (10× magnification).

The thermal compatibility between the opaque coating and porcelain veneer layer of this invention is due to several reasons including the chemical composition of materials and similar coefficient of thermal expansion (CTE) values. In general, the CTE of the opaque coating is approximately equal to or slightly lower than that of the metal substructure and is approximately equal to or slightly greater than that of the veneering porcelain.

By the term, "thermal stability" or "thermally stable" with respect to the opaque coating, it is meant that the opaque coating retains its shape and form and remains adhered to the metal substructure after multiple firings (that is, at least two and up to five firings) of the subsequently applied porcelain veneer layer at a temperature between 700° C. and 1000° C. The thermal stability of the opaque coating can be determined by examining the restoration coated with the opaque coating and porcelain veneer layer under optical microscope (10× magnification). If the opaque coating has drifted or migrated away from the metal substructure, the opaque coating is not considered to be thermally stable with the porcelain veneer layer. The porcelain veneer layer can be applied to the opaque coating by hot-pressing or manual hand-layering as described further below.

A preferred opaque porcelain composition is described in the following Table 1.

TABLE 1

CHEMICAL COMPOSITION OF OPAQUE WHITE PORCELAIN PASTE

| Oxide | Concentration Range (Wt. %) |
|---|---|
| $SiO_2$ | 42-46% |
| $Al_2O_3$ | 8-12% |
| $Na_2O$ | 2-5% |
| $K_2O$ | 6-9% |
| $Li_2O$ | 0-2% |
| CaO | 0-2% |
| MgO | 0-2% |
| $ZrO_2$ | 20-30% |
| $SnO_2$ | 1-4% |
| $Tb_4O_7$ | 0-2% |
| $CeO_2$ | 0-3% |
| $TiO_2$ | 0-2% |
| $Sb_2O_3$ | 0-0.1% |
| Fluorescing Agent | 0-5% |
| Total | 100% |

The materials of this invention, including the opaque porcelain composition, can be used with various metal copings and substructures. In general, metals and alloys and their mixtures, such as nobel alloys, palladium-based alloys, cobalt-based alloys, nickel-based alloys, pure titanium and alloys, gold-based metal-ceramic alloys, nickel chromium alloys, and the like can be used as copings and substructures. More particularly, two commercially-available alloys suitable for use are non-precious "DeguDent U" and high-noble "UltraCrown SF", both marketed by Dentsply International. These alloys can be used to make a framework by conventional casting techniques known to those skilled in the dental arts. The materials of this invention are particularly suitable for used with conventional PFM alloys, for example, having coefficients of thermal expansion (CTE) of about 14.0 ppm/° C. at 500° C.

Universal Pressable Ingots

The universal pressable ingots are used to form a dentin body layer over the opaqued metal framework in Press-to-Metal (PTM) protheses or stand-alone, all-ceramic cores using a hot-pressing technique. An appropriate amount of dentin body ingots, in either 2 gram or 5 gram size, is pressed into the prostheses mold. The shade of the dentin body ingots is selected so that the resulting layer will matches the natural color of the dentin in the patient's teeth. The pressing temperature is preferably between 700° C. and 1000° C., and more preferably between 840° C. and 940° C., and most preferably between 870° C. and 910° C. The typical pressing conditions are as follows: 700° C. (low temperature); 890° C. (high temperature); 60° C. per minute (heat rate); 20 minutes (time at high temperature); 10 to 30 minutes (pressing time) and 2.5 to 4.25 bars (pressing time). The prosthesis is then divested of the molding material for subsequent veneering porcelain application as discussed further below.

After the ingot has been pressed at a temperature in the range of 870° C. to 910° C., the pressed ingot material forms a dentin body layer that is thermally compatible with the other porcelain layers, that is, the opaque coating, and the subsequently applied veneering, and stain layers. The dentin body layer is also thermally stable when the veneering and stain layers are subsequently applied and fired.

By the term, "thermal compatibility" or "thermally compatible" with respect to the dentin body layer, it is meant that no substantial cracks are visible in the dentin body layer after the layer has been pressed at a temperature between 870° C. and 910° C. upon examining the pressed layer under an optical microscope (10× magnification); and no substantial cracks, are visible in the porcelain veneer layer after firing at a temperature between 810° C. and 860° C. upon examining the layer under an optical microscope (10× magnification).

By the term, "thermal stability" or "thermally stable" with respect to the dentin body layer, it is meant that the dentin body layer retains its shape and form and remains adhered to the opaqued metal substructure after multiple firings (that is, at least two and up to five firings) of the subsequently applied porcelain veneering layer at a temperature between 810° C. and 860° C.

A preferred ingot porcelain composition that can be used in accordance with this invention is described in the following Table 2

TABLE 2

CHEMICAL COMPOSITION OF INGOT PORCELAIN COMPOSITION FOR MAKING DENTIN BODY LAYER

| Oxide | Concentration Range (Wt. %) |
|---|---|
| $SiO_2$ | 63-66% |
| $Al_2O_3$ | 10-14% |
| $Na_2O$ | 3-7% |
| $K_2O$ | 9-12% |
| $Li_2O$ | 0-2% |
| CaO | 1-4% |
| BaO | 0-3% |
| $Tb_4O_7$ | 0-2% |
| $CeO_2$ | 0-2% |
| Total | 100% |

Universal Veneering Porcelain

The universal veneering porcelain composition is used to form a veneer layer over the opaqued metal substructure or all ceramic core. The veneering porcelain composition is applied to the dental prosthesis to form a dentin-enamel layer (PFM applications where a dentin body layer has not been formed previously) or enamel layer (PTM and all-ceramic applications where a dentin body layer has been formed previously.) After the composition has been fired to a temperature in the range of 800° to 850° C., the coating forms a hard and durable layer having a shade that matches the shade and translucency of the patient's natural teeth. The resulting layer is thermally compatible and thermally stable with the opaqued metal substructure and all-ceramic core.

By the term, "thermal compatibility" or "thermally compatible" with respect to the veneering porcelain dentin-enamel or enamel layer, it is meant that no substantial cracks are visible in the dentin-enamel or enamel layer after the layer has been fired at a temperature between 810° C. and 860° C. upon examining the fired layer under an optical microscope at 10× magnification; and no substantial cracks, are visible in the dentin body layer after pressing at a temperature between 870° C. and 910° C. upon examining the layer under an optical microscope at 10× magnification.

By the term, "thermal stability" or "thermally stable" with respect to the veneering porcelain dentin-enamel or enamel layer, it is meant that the dentin-enamel or enamel layer retains its shape and form and remains adhered to either the opaqued metal substructure or dentin body layer after firing the subsequently applied shade stain and glaze overlayer at a temperature between 780° C. and 840° C.

A preferred veneering porcelain composition is described in the following Table 3.

TABLE 3

CHEMICAL COMPOSITION OF INGOT VENEERING PORCELAIN FOR MAKING DENTIN-ENAMEL OR ENAMEL LAYERS

| Oxide | Concentration Range (Wt. %) |
|---|---|
| $SiO_2$ | 62-65% |
| $Al_2O_3$ | 8-11% |
| $Na_2O$ | 8-11% |
| $K_2O$ | 4-7% |
| $Li_2O$ | 0-2% |
| CaO | 2-5% |
| BaO | 0-3% |
| MgO | 1-4% |
| $SnO_2$ | 0-2% |
| $Tb_4O_7$ | 0-2% |
| $CeO_2$ | 0-2% |
| $Sb_2O_3$ | 0-2% |
| $P_2O_5$ | 0-0.1% |
| $TiO_2$ | 0-0.1% |
| F | 0-1% |
| Total | 100% |

In addition, a one-step fired shade stain material paired with a glaze porcelain material can be applied over PTM and/or all-ceramic full-contour crowns and bridges made with full-contour technique to complete the restoration. The shade stain porcelain composition provides the restoration with the proper color shade so that the restoration matches the color shade of neighboring teeth. Meanwhile, the glaze porcelain provides the restoration with a hard and smooth film coating. The finished restoration has a shiny and glossy appearance after the shade stain and glaze materials have been applied. The shade stain and glaze are separate and distinct materials, but they are normally applied together and are collectively and singularly referred to herein as forming an overlayer. Once the shade stain and porcelain materials are applied, they are fired in a single step. The firing temperature of the shade stain and glaze overlayer is preferably between 750° C. and 950° C., more preferably between 800° C. and 900° C., and most preferably between 780° C. and 840° C. It is also recognized that, the same glaze porcelain can be applied over PFM, incisal cutback PTM and/or all-ceramic cores to complete these restorations. In the case of PFM, incisal cutback PTM and/or all-ceramic cores, it is not necessary to apply the shade stain porcelain material, because these products are already shaded. Additional shade stain does not need to be applied to these restorations. The components used to make the shade stain and glaze porcelain materials are listed generally in the following Table 4. It should be understood that the shade stain composition will differ from the glaze porcelain composition in view of the different oxides and/or weight percentage of ingredients used in the respective compositions.

TABLE 4

COMPONENTS USED IN SHADE STAIN AND GLAZE PORCELAIN MATERIALS

| Oxide | Concentration Range (Wt. %) |
|---|---|
| $SiO_2$ | 56-64% |
| $Al_2O_3$ | 6-13% |
| $Na_2O$ | 7-15% |
| $K_2O$ | 7-15% |
| $Li_2O$ | 0-5% |
| CaO | 0-3% |
| MgO | 2-5% |
| $SnO_2$ | 0-4% |
| $Tb_4O_7$ | 0-3% |
| $CeO_2$ | 0-2% |
| $B_2O_3$ | 0-5% |
| $Sb_2O_3$ | 0-0.5% |
| F | 0-2.5% |
| $TiO_2$ | 0-1% |
| Total | 100% |

Referring now to the Figures, the dental prostheses made in accordance with this invention are shown in detail. FIG. 1 shows a crown (8) made by a porcelain fused-to-metal (PFM) process is shown positioned on a die model (10). The crown includes a metal coping or substructure (12) which is coated with a universal opaquing porcelain layer (14), universal dentin veneering porcelain layer (16), universal enamel veneering porcelain layer (18), and overglaze porcelain layer (20).

Figure 2:
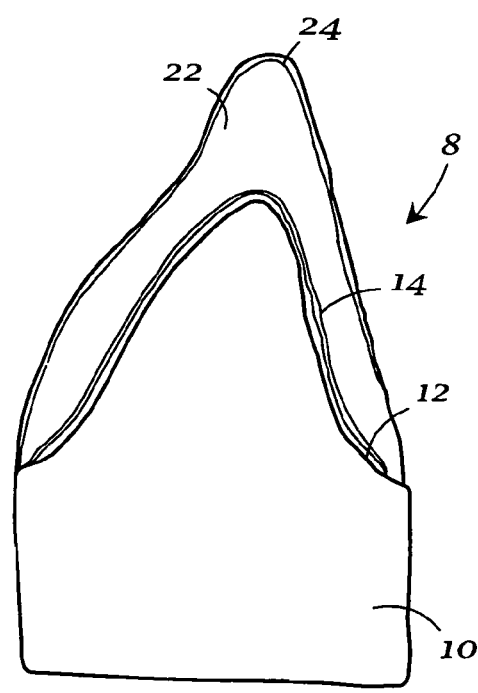
FIG. 2 is a cross-sectional schematic view of a full-contour PTM crown on a die model fabricated with components in accordance with the invention.

FIG. 2 shows a PTM crown (8) made using a full-contour technique on a die model (10). The crown (8) has a metal coping (12) with a universal opaquing porcelain (14), universal pressable ingot that forms a dentin body layer (22), and a shade stain/glaze porcelain (24).

Figure 3:
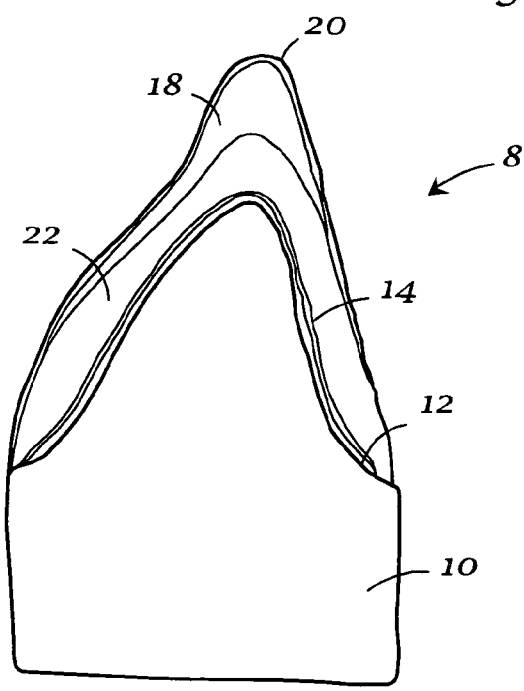
FIG. 3 is a cross-sectional schematic view of an incisal cutback PTM crown on a die model fabricated with components in accordance with the invention.

FIG. 3 shows a PTM crown (8) made using an incisal cutback technique on a die model 10. The crown (8) has a metal coping (12) with a universal opaquing porcelain (14), universal pressable ingot that forms a dentin body layer (22), universal enamel veneering porcelain (18), and overglaze porcelain (20).

Figure 4:
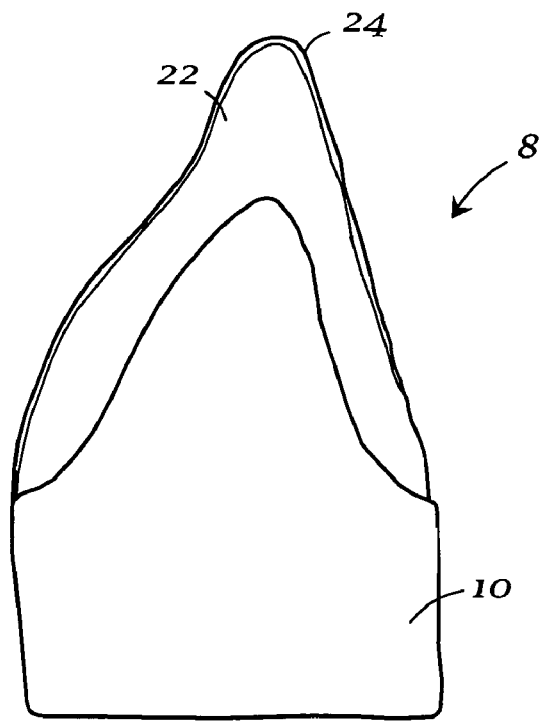
FIG. 4 is a cross-sectional schematic view of a full-contour, pressed all-ceramic crown on a die model fabricated with components in accordance with the invention.

FIG. 4 shows an all-ceramic crown (8) made using a full-contour technique on a die model (10). The crown (8) has an all-ceramic coping pressed using a universal pressable ingot that forms a dentin body layer (22), and shade stain/glaze porcelain (24).

Figure 5:
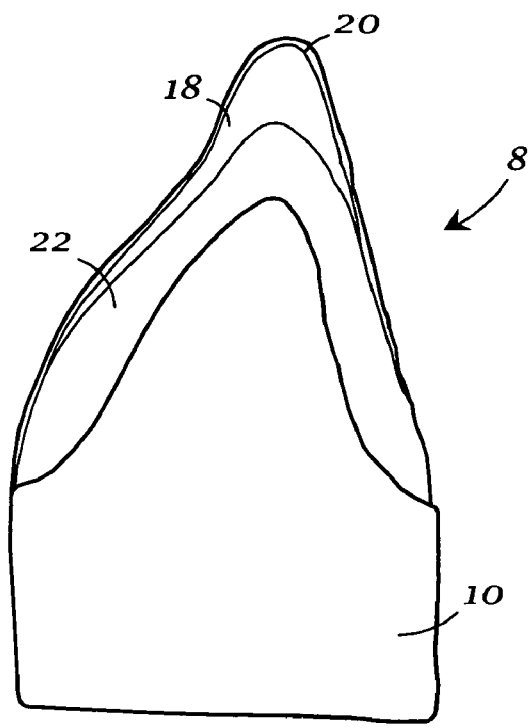
FIG. 5 is a cross-sectional schematic view of an incisal cutback, pressed all-ceramic crown on a die model fabricated with components in accordance with the invention.

FIG. 5 shows an all-ceramic crown (8) made using an incisal cutback technique on a die model (10). The crown (8) has an all-ceramic coping pressed using a universal pressable ingot that forms a dentin body layer (22); a universal enamel veneering porcelain that forms an enamel layer (18); and overglaze porcelain (20).

Figure 6:
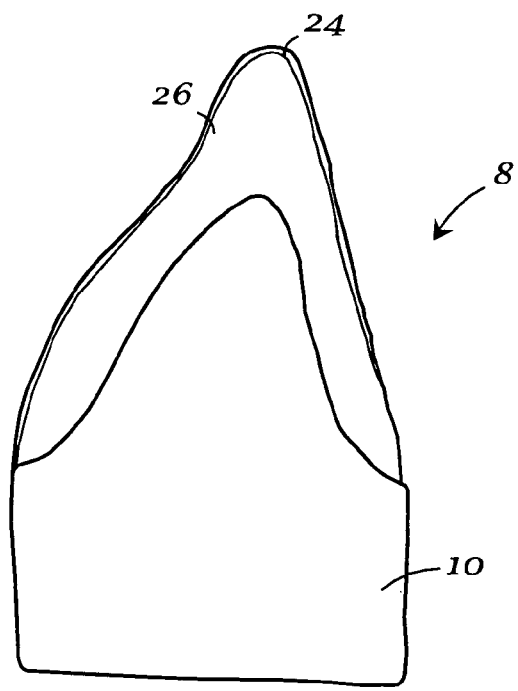
FIG. 6 is a cross-sectional schematic view of a full-contour, CAM-machined all-ceramic crown on a die model fabricated with components in accordance with the invention.

FIG. 6 shows an all-ceramic crown (8) made using a machinable block on a die model (10). The crown (8) has an all-ceramic full-contour coping machined using machinable block (26) with a shade stain/glaze porcelain 24.

Figure 7:
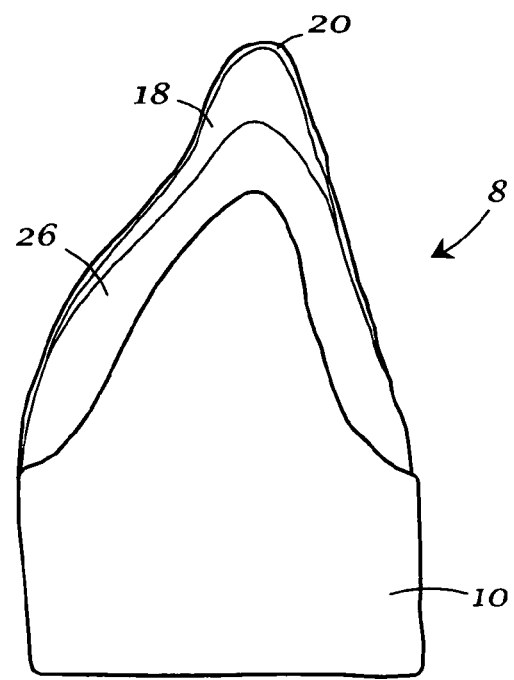
FIG. 7 is a cross-sectional schematic view of an incisal build-up, CAM-machined all-ceramic crown on a die model fabricated with components in accordance with the invention.

FIG. 7 shows an all-ceramic crown (8) made using machinable block on a die model (10). The crown (8) has an all-ceramic coping machined using machinable block (26); a universal enamel veneering porcelain that forms an enamel layer (18); and overglaze porcelain (20).

The finished restoration made in accordance with this invention can be subjected to a "thermal shock" test to further evaluate its thermal properties. In this test, the finished restoration is heated to a given temperature in a furnace. After the restoration has been removed, it is quenched into iced water (normally having a temperature between 0° C. and 5° C.).

Then, the restoration is examined under an optical microscope (10× magnification) to determine if any cracks have formed in the restoration. For example, the restoration can be heated to 80° C. in the furnace, removed, and quenched in cool water. If no cracks are visible upon microscopic examination, the restoration is placed back in the furnace and heated to a higher temperature. Normally, the temperature is incrementally increased by ten degrees (10° C.). Thus, the restoration is heated to 90° C. in the furnace, removed, and quenched in cool water. The restoration is microscopically examined for cracks. This sequence of heating and quenching is repeated until the critical quenching temperature (temperature at which cracks first appear) is determined. Preferably, both single unit crowns and three-unit bridges made in accordance with this invention have a critical quenching temperature of about 110° C.

Physical/Mechanical Properties

The physical/mechanical properties of the integrated dental porcelain system of this invention are described in the following Table 5. The components were tested for different properties according to the methods described in ISO 6872 (1995-09-01) for dental porcelains and ISO 9693 (1999) for metal-ceramic dental restorative systems. The components meet all ISO requirements as shown in Table 5.

TABLE 5

PHYSICAL/MECHANICAL PROPERTIES OF INTEGRATED DENTAL PORCELAIN SYSTEM

| Property | ISO Requirement | Universal Opaque | Universal dentin/ enamel | Universal Ingot | machinable block all- ceramic |
|---|---|---|---|---|---|
| Flexural strength (MPa) | 50 (PFM/PTM) 100 (all-ceramic core) | 162 | 80 | 135 | 115 |
| Thermal expansion coefficient @ 25-500° C. (ppm/° C.) | ±0.5 (2x & 4x - applies to opaque & dentin) | 12.9 ± 0.4 (as-sintered) 13.1 ± 0.4 (simulated pressing) | 12.1 ± 0.4 (@ 25-480° C.) | 12.0 ± 0.4 (as-sintered) 13.0 ± 0.4 (simulated pressing) | 12.5 ± 0.4 |
| Glass transition temperature (° C.) | ±20 | 540 ± 20 | 500 ± 20 | 600 ± 20 | 575 ± 20 |
| Chemical solubility (μg/cm$^2$) | 100 (dentin & opaque) 2,000 (ingot & machinable block) | 17.7 | 22.6 | 33.1 | 40.4 |

The integrated dental porcelain system of the present invention is designed for making PFM, PTM, and all-ceramic restorations in a simplified manner. As described above, the system includes three major universal components: opaque coating, dentin/enamel porcelain, and pressable ingots that can be used interchangeably. For example, the same pressing temperature and same ingot can be used to press either the dentin body when making a PTM restoration and/or all-ceramic core. Furthermore, the same firing temperature and the same opaque coating can be used to overlay metal substructures for making PFM and/or PTM restorations. And, the same firing temperature and same dentin/enamel porcelain can be used to veneer over an opaqued metal substructure for making PFM restorations and/or it can be used to veneer over either pressed and/or machined all-ceramic cores for making all-ceramic restorations.

It should be understood that while the present invention has been described in considerable detail with respect to certain specific embodiments thereof, it should not be considered limited to such embodiments but may be used in other ways without departing from the spirit of the invention and scope of the appended claims.

What is claimed is:
1. A kit for making a dental prosthesis, comprising:
a) an opaque composition comprising:

| Components | Concentration Range (Wt. %) |
|---|---|
| SiO$_2$ | 42-46% |
| Al$_2$O$_3$ | 8-12% |
| Na$_2$O | 2-5% |
| K$_2$O | 6-9% |
| Li$_2$O | 0-2% |
| CaO | 0-2% |
| MgO | 0-2% |
| ZrO$_2$ | 20-30% |
| SnO$_2$ | 1-4% |
| Tb$_4$O$_7$ | 0-2% |
| CeO$_2$ | 0-3% |
| TiO$_2$ | 0-2% |
| Sb$_2$O$_3$ | 0-0.1% |
| Fluorescing agent | 0-5% | b) an ingot porcelain composition comprising:

| Oxide | Concentration Range (Wt. %) |
|---|---|
| SiO$_2$ | 63-66% |
| Al$_2$O$_3$ | 10-14% |
| Na$_2$O | 3-7% |
| K$_2$O | 9-12% |
| Li$_2$O | 0-2% |
| CaO | 1-4% |
| BaO | 0-3% |
| Tb$_4$O$_7$ | 0-2% |
| CeO$_2$ | 0-2%; and | c) a veneering porcelain composition comprising:

| Oxide | Concentration Range (Wt. %) |
|---|---|
| SiO$_2$ | 62-65% |
| Al$_2$O$_3$ | 8-11% |

-continued

| Oxide | Concentration Range (Wt. %) |
|---|---|
| $Na_2O$ | 8-11% |
| $K_2O$ | 4-7% |
| $Li_2O$ | 0-2% |
| CaO | 2-5% |
| BaO | 0-3% |
| MgO | 1-4% |
| $SnO_2$ | 0-2% |
| $Tb_4O_7$ | 0-2% |
| $CeO_2$ | 0-2% |
| $Sb_2O_3$ | 0-2% |
| $P_2O_5$ | 0-0.1% |
| $TiO_2$ | 0-0.1% |
| F | 0-1%. |

2. The kit of claim 1, wherein the opaque composition is used to coat a metal substructure, the composition being fired at a temperature in the range of about 860° to about 900° C. and having a coefficient of thermal expansion ranging from 12.5 to 13.5 ppm/° C., measured between 25° C. and 500° C.

3. The kit of claim 1, wherein the ingot porcelain composition is used to form a dentin body layer by hot-pressing, the composition being pressed at a temperature in the range of about 870° to about 910° C. and the composition after pressing, having a coefficient of thermal expansion ranging from 11.6 to 12.5 ppm/° C., measured between 25° C. and 500° C.

4. The kit of claim 1, wherein the veneering porcelain composition is used to form a dentin-enamel layer over an opaqued metal substructure, the composition being fired at a temperature in the range of about 810° to about 860° C. and the composition, upon being fired, having a coefficient of thermal expansion ranging from 11.7 to 12.5 ppm/° C., measured between 25° C. and 480° C.

5. The kit of claim 1, wherein the veneering porcelain composition is used to form an enamel layer over an all-ceramic core containing a porcelain dentin body layer, the composition being fired at a temperature in the range of about 810° to about 860° C. and the composition, upon being fired, having a coefficient of thermal expansion ranging from 11.7 to 12.5 ppm/° C., measured between 25° C. and 480° C.

6. The kit of claim 1, further comprising a shade stain and a glaze composition for being applied over a pressed dentin body layer to form an overlayer, the shade stain and the glaze compositions, each comprising the following components:

| Oxide | Concentration Range (Wt. %) |
|---|---|
| $SiO_2$ | 56-64% |
| $Al_2O_3$ | 6-13% |
| $Na_2O$ | 7-15% |
| $K_2O$ | 7-15% |
| $Li_2O$ | 0-5% |
| CaO | 0-3% |
| MgO | 2-5% |
| $SnO_2$ | 0-4% |
| $Tb_4O_7$ | 0-3% |
| $CeO_2$ | 0-2% |
| $B_2O_3$ | 0-5% |
| $Sb_2O_3$ | 0-0.5% |
| F | 0-2.5% |
| $TiO_2$ | 0-1% | wherein the compositions, after firing to a temperature in the range of about 780° to about 840° C., form a shade stain and glaze overlayer over the pressed dentin body layer, the shade stain and glaze overlayer being thermally compatible and thermally stable with the pressed dentin body layer.

7. The kit of claim 1, wherein the opaque composition is in powder or paste form prior to being fired.

8. The kit of claim 1, further comprising a glaze composition for being applied over a fired dentin-enamel layer to form an overlayer, the glaze composition comprising the following components:

| Oxide | Concentration Range (Wt. %) |
|---|---|
| $SiO_2$ | 56-64% |
| $Al_2O_3$ | 6-13% |
| $Na_2O$ | 7-15% |
| $K_2O$ | 7-15% |
| $Li_2O$ | 0-5% |
| CaO | 0-3% |
| MgO | 2-5% |
| $SnO_2$ | 0-4% |
| $Tb_4O_7$ | 0-3% |
| $CeO_2$ | 0-2% |
| $B_2O_3$ | 0-4%. |

9. The kit of claim 8, wherein the glaze composition, after firing to a temperature in the range, of about 780° to about 840° C., forms a glaze overlayer over a fired dentin-enamel layer, the glaze overlayer being thermally compatible with a dentin-enamel layer.

10. The kit of claim 1, further comprising a shade stain and a glaze composition for being applied over a pressed dentin body layer to form an overlayer, the shade stain and the glaze compositions, each comprising the following components:

| Oxide | Concentration Range (Wt. %) |
|---|---|
| $SiO_2$ | 56-64% |
| $Al_2O_3$ | 6-13% |
| $Na_2O$ | 7-15% |
| $K_2O$ | 7-15% |
| $Li_2O$ | 0-5% |
| CaO | 0-3% |
| MgO | 2-5% |
| $SnO_2$ | 0-4% |
| $Tb_4O_7$ | 0-3% |
| $CeO_2$ | 0-2% |
| $B_2O_3$ | 0-4% |
| $Sb_2O_3$ | 0-0.5% |
| F | 0-2.5% |
| $TiO_2$ | 0-1%. |

11. The kit of claim 1, wherein:
(i) the opaque composition, after firing to a temperature in the range of about 800° to about 1000° C., has flexural strength of 162 MPa;
(ii) the porcelain composition, after pressing at a temperature in the range of about 870° C. to about 910° C., has flexural strength of 135 MPa;
(iii) the veneering porcelain composition, after firing at a temperature in the range of about 810° C. to about 860° C., has flexural strength of 80 MPa; or
(iv) any combination of (i), (ii), and (iii).

* * * * *